United States Patent
Kobayashi et al.

(10) Patent No.: US 10,507,099 B2
(45) Date of Patent: Dec. 17, 2019

(54) INTRAOCULAR LENS INSERTION APPARATUS

(71) Applicant: KOWA COMPANY, LTD., Nagoya-shi, Aichi (JP)

(72) Inventors: Kenichi Kobayashi, Nagoya (JP); Shuji Abe, Nagoya (JP); Genyo Midorikawa, Nagoya (JP)

(73) Assignee: Kowa Company, Ltd., Nagoya-shi (JP)

( * ) Notice: Subject to any disclaimer, the term of this patent is extended or adjusted under 35 U.S.C. 154(b) by 230 days.

(21) Appl. No.: 15/527,563

(22) PCT Filed: Nov. 19, 2015

(86) PCT No.: PCT/JP2015/082586
§ 371 (c)(1),
(2) Date: May 17, 2017

(87) PCT Pub. No.: WO2016/080497
PCT Pub. Date: May 26, 2016

(65) Prior Publication Data
US 2017/0319331 A1    Nov. 9, 2017

(30) Foreign Application Priority Data
Nov. 19, 2014    (JP) ................. 2014-234887

(51) Int. Cl.
*A61F 2/16*    (2006.01)
(52) U.S. Cl.
CPC ............... *A61F 2/167* (2013.01); *A61F 2/16* (2013.01); *A61F 2250/0097* (2013.01)

(58) Field of Classification Search
CPC .......... A61F 2/16; A61F 2/167; A61F 2/1662; A61F 2/1664
See application file for complete search history.

(56) References Cited

U.S. PATENT DOCUMENTS

| | | |
|---|---|---|
| 2003/0187455 A1 | 10/2003 | Kobayashi et al. |
| 2003/0212406 A1 | 11/2003 | Kobayashi et al. |
| 2009/0171366 A1 | 7/2009 | Tanaka |

(Continued)

FOREIGN PATENT DOCUMENTS

| | | |
|---|---|---|
| CN | 1448115 A | 10/2003 |
| CN | 1456134 A | 11/2003 |

(Continued)

OTHER PUBLICATIONS

Office Action received in connection with Chinese Patent Application No. 201580063103.5 dated Jun. 5, 2018.

(Continued)

*Primary Examiner* — Tuan V Nguyen
(74) *Attorney, Agent, or Firm* — Knobbe, Martens, Olson & Bear, LLP

(57) ABSTRACT

An intraocular lens insertion apparatus includes a distal end member which is inserted through an incision in an eyeball of a patient, an opening member provided for the distal end member through which an intraocular lens is ejected, and an indicator provided for the distal end member. The indicator is used for indicating that an entire part of the opening member is inside a cornea of the eyeball or inside a sclerocornea of the eyeball with respect to an external flap of the incision.

3 Claims, 14 Drawing Sheets

(56) References Cited

U.S. PATENT DOCUMENTS

| | | | |
|---|---|---|---|
| 2013/0012956 A1* | 1/2013 | Mirlay | A61F 2/167 606/107 |
| 2013/0331853 A1 | 12/2013 | Marunaka et al. | |
| 2015/0313709 A1 | 11/2015 | Kobayashi | |

FOREIGN PATENT DOCUMENTS

| | | |
|---|---|---|
| CN | 101467925 A | 7/2009 |
| EP | 1 800 623 A1 | 6/2007 |
| EP | 2 074 962 A1 | 7/2009 |
| EP | 2 123 240 A1 | 11/2009 |
| JP | 2002-136538 A | 5/2002 |
| JP | 2009-160151 A | 7/2009 |
| JP | 2012-125361 A | 7/2012 |
| WO | WO 2012/086797 A1 | 6/2012 |
| WO | WO 2014/084355 A1 | 6/2014 |

OTHER PUBLICATIONS

Extended European Search Report received in European Patent Application No. 15860597.2 dated Jun. 8, 2018.
International Search Report for International Application No. PCT/JP2015/082586, dated Feb. 16, 2016.

\* cited by examiner

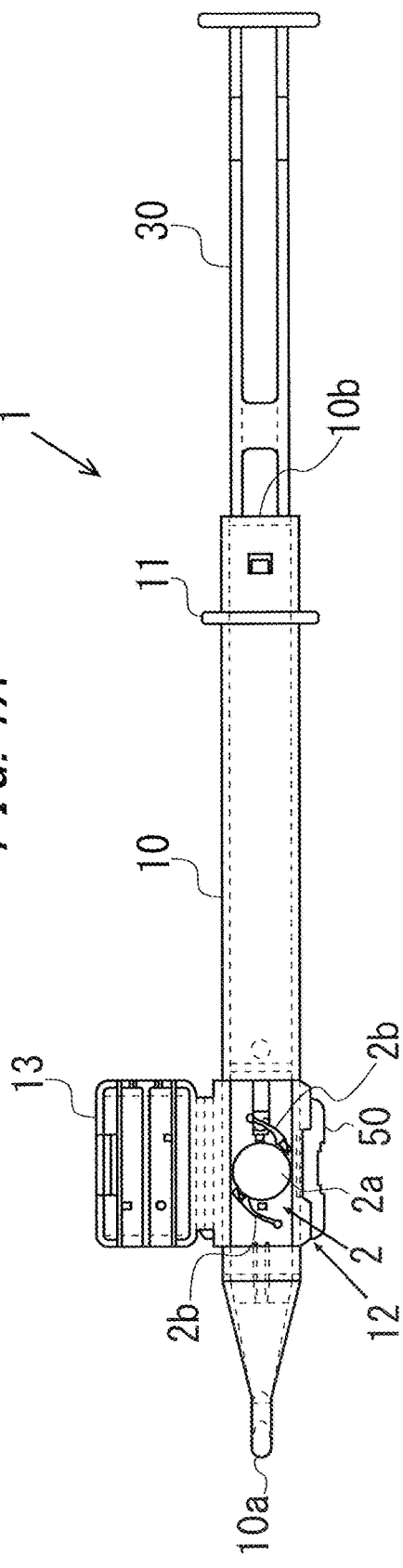
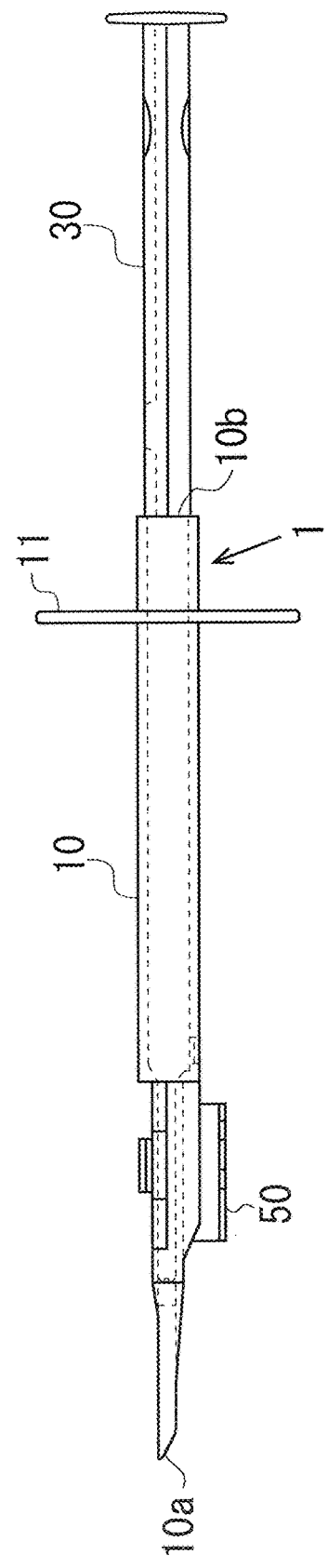

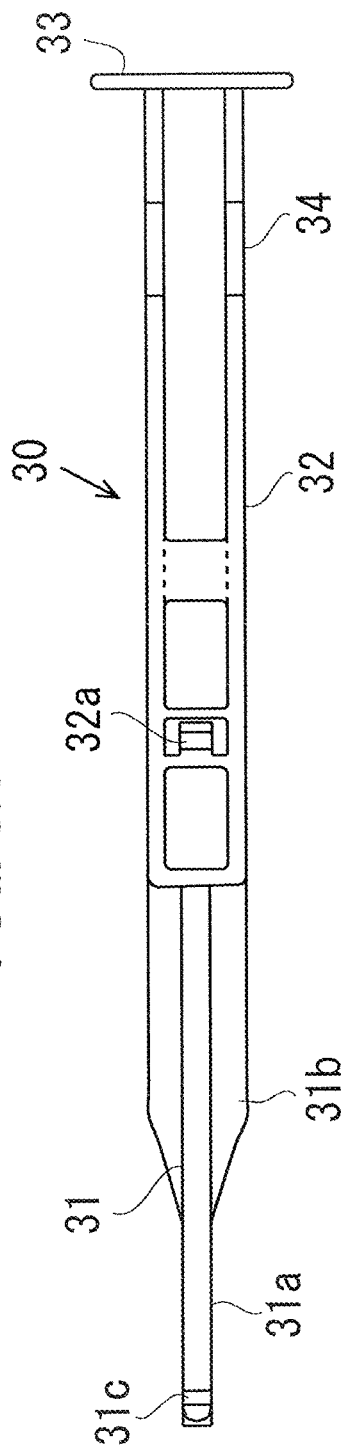
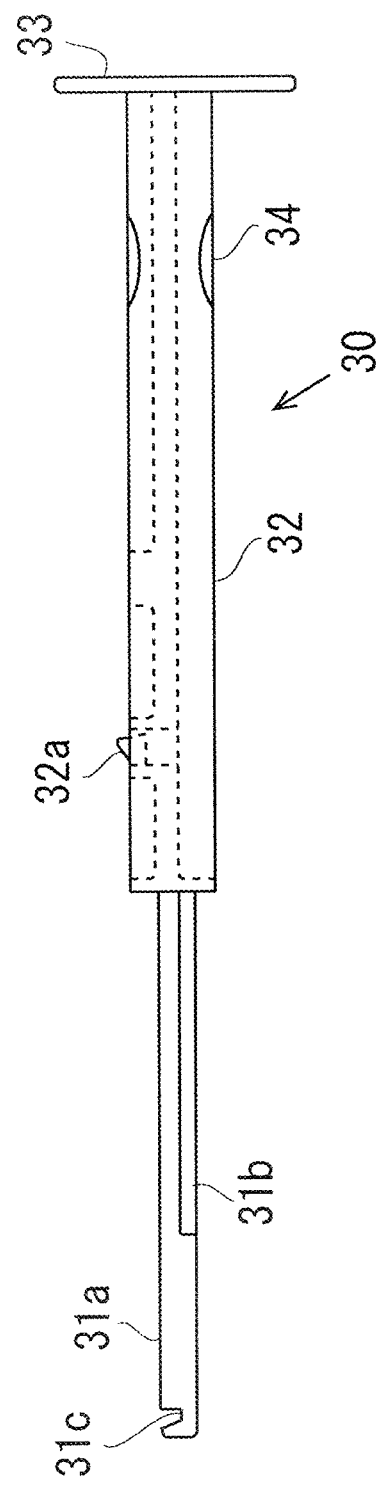
FIG. 5A
FIG. 5B

INTRAOCULAR LENS INSERTION APPARATUS

CROSS-REFERENCE TO RELATED APPLICATION

This application is the U.S. National Phase under 35 U.S.C. § 371 of International Application PCT/JP2015/082586, filed Nov. 19, 2015, which is based upon and claims the benefit of priority of the prior Japanese Patent Application No. 2014-234887, filed on Nov. 19, 2014, the entire contents of which are incorporated herein by reference.

FIELD

The embodiments discussed herein relate to an intraocular lens insertion apparatus.

BACKGROUND

Intraocular lenses are widely used to be replaced with human opacity crystalline lenses in cataract treatments to compensate the optical powers of the lenses. In intraocular lens insertion surgeries for the cataract treatments, an incision (discission cut) which is several millimeters in length is produced at the edge of the cornea or the sclerocornea, the human crystalline lens is crushed and removed by phacoemulsification and aspiration etc. and the intraocular lens is inserted and fixed in the eye using an intraocular lens insertion apparatus, for example.

Recently, it is considered as desirable to produce an incision with a smaller in size in view of the burden on a patient etc. In addition, it is also desirable to reduce the length of the distal end member of the intraocular lens insertion apparatus inserted through the incision into the eyeball of the patient. Therefore, an indicator showing the insertion length of the intraocular lens insertion apparatus into the eyeball is proposed (See Patent Literature 1).

CITATION LIST

Patent Literature

[PTL 1] JP-A-2002-136538

SUMMARY

Technical Problem

When a part of the opening member for ejecting the intraocular lens of the intraocular lens insertion apparatus is outside what is called an external flap of the incision, an abnormal behavior of the intraocular lens occurs and the intraocular lens is not inserted into the eyeball normally. The indicator provided for the intraocular lens insertion apparatus as described above can be used to prevent the intraocular lens from being ejected in an abnormal direction. However, the indicator cannot be used for determining whether the opening member is outside the external flap of the incision. Therefore, an abnormal behavior of the intraocular lens may occur even when the above indicator is used.

The technique of this disclosure has been made in view of the above-mentioned circumstances, and it is an object of this disclosure to provide an intraocular lens insertion apparatus with which the insertion length of the apparatus inserted through the incision produced in the cornea or the sclerocornea of the patient can be controlled.

Solution to Problem

According to the embodiments described herein, it is provided an intraocular lens insertion apparatus including a distal end member which is inserted through an incision produced on an eyeball of a patient, an opening member provided for the distal end member through which an intraocular lens is ejected, and an indicating means provided for the distal end member for indicating that an entire part of the opening member is inside a cornea of the eyeball or inside a sclerocornea of the eyeball with respect to an external flap of the incision. With such a configuration, when the user inserts the intraocular lens insertion apparatus through the incision, the user can use the indicating means to determine that the entire part of the opening member is inside the cornea or the sclerocornea with respect to the external flap of the incision even if the visibility of the opening member is lowered. Thus, the user can easily control the insertion length of the intraocular lens insertion apparatus to prevent an abnormal behavior of the intraocular lens when the intraocular lens is ejected from the intraocular lens insertion apparatus. In addition, the intraocular lens insertion apparatus as above can be configured so that the indicating means indicates that the entire part of the opening member is inside the cornea of the eyeball or inside the sclerocornea of the eyeball based on a relation, regarding a part of the distal end member inserted through the incision which projects from an internal flap of the incision, between an length of the distal end member in an insertion direction of the distal end member and an insertion length of the distal end member in a direction perpendicular to the insertion direction in a top view of the distal end member in a direction of an optical axis of the intraocular lens set in the intraocular lens insertion apparatus. With such a configuration, when the user inserts the intraocular lens insertion apparatus into the eyeball through the incision, the user can control the insertion length of the intraocular lens insertion apparatus to prevent the abnormal behavior of the intraocular lens according to the shape of the distal end member projecting from the internal flap of the incision in the top view of the distal end member of the intraocular lens insertion apparatus.

In addition, the above intraocular lens insertion apparatus can be configured so that the indicating means indicates that the entire part of the opening member is inside the cornea of the eyeball or inside the sclerocornea of the eyeball with respect to the external flap of the incision when the length of the distal end member in the insertion direction is longer than the length of the distal end member in the direction perpendicular to the insertion direction. Alternately, the above intraocular lens insertion can be configured so that the indicating means is an indicator provided for a surface of the distal end member, and when the distal end member is inserted through the incision, the entire part of the opening member is inside the cornea or inside the sclerocornea with respect to the external flap of the incision in a state in which the indicator provided for the distal end member almost overlaps the internal flap of the incision or is inside the internal flap in the top view.

Advantageous Effects of Invention

According to the technique disclosed herein, it is possible to provide an intraocular lens insertion apparatus with which the insertion length of the apparatus inserted through the incision produced in the cornea or the sclerocornea of the patient can be controlled.

BRIEF DESCRIPTION OF DRAWINGS

FIG. 1A A diagram illustrating the schematic configuration of an intraocular lens insertion apparatus according to one embodiment.

FIG. 1B A diagram illustrating the schematic configuration of the intraocular lens insertion apparatus in FIG. 1A according to one embodiment.

FIG. 5A A diagram illustrating the schematic configuration of a plunger according to one embodiment.

FIG. 5B A diagram illustrating the schematic configuration of the plunger in FIG. 5A according to one embodiment.

DESCRIPTION OF EMBODIMENTS

Figure 2A:
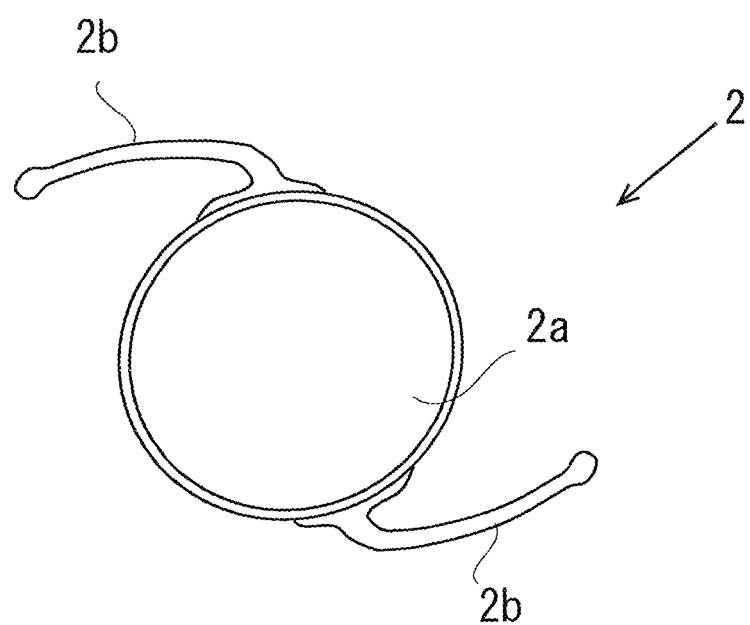
FIG. 2A A diagram illustrating the schematic configuration of an intraocular lens according to one embodiment.

Hereinafter, embodiments of the present invention are described with reference to drawings.

First Embodiment

FIG. 1A and FIG. 1B illustrate a schematic configuration of an intraocular lens insertion apparatus 1 according to the first embodiment. FIG. 1A illustrates a plan view of the intraocular lens insertion apparatus 1 in a state where a stage lid member 13 is opened. FIG. 1B illustrates a side view of the intraocular lens insertion apparatus 1 in a state where the stage lid member 13 is closed. The insertion apparatus 1 includes a nozzle body 10 which forms an apparatus body, a plunger 30 which forms a push member for pushing an intraocular lens, and a stage member 12 and the stage lid member 13 which form an accommodating member for accommodating an intraocular lens. The stage member 12 is integrally or independently formed on the nozzle body 10. The plunger 30 is inserted into the nozzle body 10. An intraocular lens 2 is set on the stage member 12. The stage member 12 is integrally formed with the stage lid member 13.

The nozzle body 10 of the intraocular lens insertion apparatus 1 is formed in a tubular shape the cross section of which is a rectangle. An opening formed at one end of the nozzle body 10 (referred to as a rear end member 10b) is larger than an opening formed at the other end of the nozzle body 10 which is referred to as a distal end member 10a. The plunger 30 is inserted into the nozzle body 10 and can be moved to-and-fro in the nozzle body 10.

In the descriptions hereinafter, the direction extending toward the distal end member 10a from the rear end member 10b of the nozzle body 10 is assumed as the frontward direction, the direction opposite to the frontward direction is assumed as the rearward direction, the direction toward a viewer's side with respect to a paper surface on which FIG. 1A is drawn is assumed as the upward direction, the direction opposite to the upward direction is assumed as the downward direction, the direction toward a viewer's side with respect to a paper surface on which FIG. 1B is drawn is assumed as the leftward direction, and the direction opposite to the leftward direction is assumed as the rightward direction. In this case, an upper side corresponds to a front side along an optical axis of a lens body 2a described later, a lower side corresponds to a rear side along the optical axis of the lens body 2a, a front side corresponds to a front side in the pushing direction of the plunger 30, and a rear side corresponds to a rear side in the pushing direction of the plunger 30.

A hold member 11 which projects in a plate shape and on which a user hooks his fingers when he pushes the plunger 30 toward the distal end side of the nozzle body 10 is integrally formed on the nozzle body 10 in the vicinity of the rear end member 10b of the nozzle body 10. The stage member 12 on which the intraocular lens 2 is to be set is formed on the rear side of the nozzle body 10. The stage member 12 is configured such that an upper side of the nozzle body 10 is opened by opening the stage lid member 13. The positioning member 50 is mounted on the stage member 12 from below the nozzle body 10. With the use of the positioning member 50, the intraocular lens 2 is stably held on the stage member 12 even before the insertion apparatus 1 is used (during transportation).

That is, in the intraocular lens insertion apparatus 1, at the time of manufacturing the intraocular lens insertion apparatus 1, the intraocular lens 2 is set on the stage member 12 such that a front side along an optical axis is directed upward in a state where the stage lid member 13 is opened and the positioning member is mounted on the stage member 12. Then, the intraocular lens insertion apparatus 1 is shipped after the stage lid member 13 is closed, and the insertion apparatus 1 is sold. Then, a user removes the positioning member 50 while holding the stage lid member 13 in a closed state and, thereafter, pushes the plunger 30 toward the distal end side of the nozzle body 10. Due to such an operation, the intraocular lens 2 is pushed by the plunger 30, and the intraocular lens 2 is ejected into the inside of the eyeball from the distal end member 10a. In the insertion apparatus 1, the nozzle body 10, the plunger 30, and the positioning member 50 are formed using a resin such as polypropylene. Polypropylene has been proven as a material used for medical apparatuses. In addition, polypropylene is reliable in chemical resistance etc.

Figure 2B:
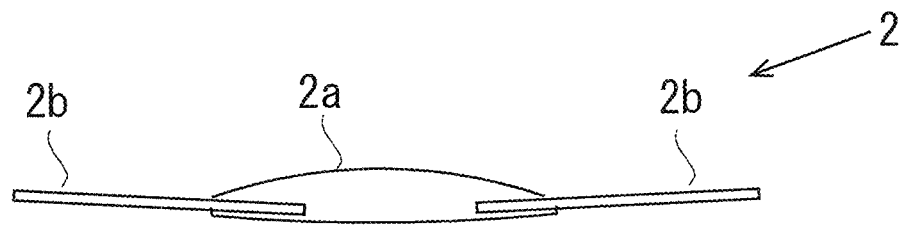
FIG. 2B A diagram illustrating the schematic configuration of the intraocular lens in FIG. 2A according to one embodiment.

FIG. 2A and FIG. 2B are diagrams illustrating the schematic configuration of the intraocular lens 2. FIG. 2A is a diagram illustrating a plan view, and FIG. 2B is a diagram illustrating a side view. The intraocular lens 2 is what is called a one-piece type intraocular lens. Although the following descriptions assume that the intraocular lens 2 is the one-piece type intraocular lens, the present invention is also applicable to what is called a three-piece type intraocular lens instead of the one-piece type intraocular lens. The intraocular lens 2 is formed of the lens body 2a having a predetermined refractivity, and two plate-like support members 2b which are connected to the lens body 2a and are provided for holding the lens body 2a inside of the eyeball.

Figure 3:
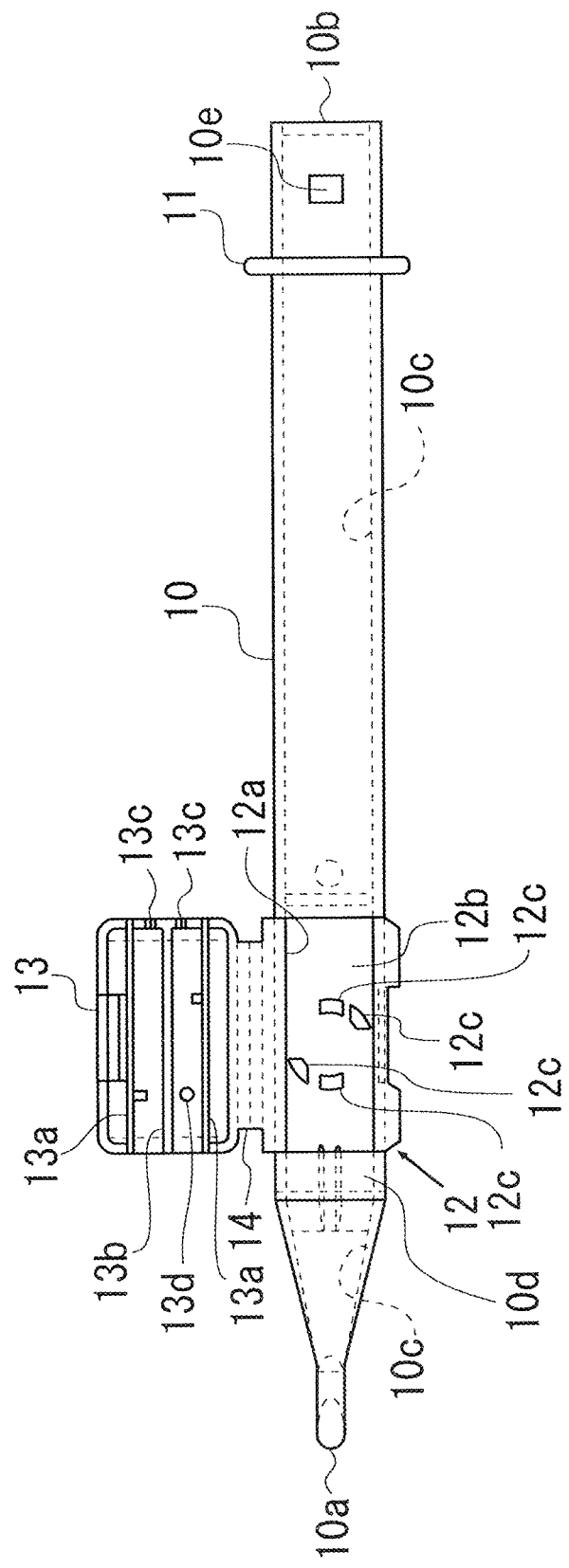
FIG. 3 A diagram illustrating the schematic configuration of a nozzle body according to one embodiment.

FIG. 3 is a plan view of the nozzle body 10. As illustrated in FIG. 1 as above, in the nozzle body 10, the intraocular lens 2 is set on the stage member 12. In such a state, the intraocular lens 2 is pushed by the plunger 30, and is ejected from the distal end member 10a. Here, a through-hole 10c whose cross-sectional shape changes corresponding to a change in a profile of the nozzle body 10 is formed inside of the nozzle body 10. Although the cross section of the through-hole is illustrated as an oval shape (egg shape) in the diagrams, the shape of the cross section of the through-hole can be changed to a circle shape or an ellipse shape according to the shape of the specification of an intraocular lens. It is noted that the through-hole is an example of a path of an insertion used for inserting an intraocular lens into the eyeball. In the ejection of the intraocular lens 2, the intraocular lens 2 is deformed corresponding to a change in a cross-sectional shape of the through-hole 10c formed inside of the nozzle body 10, and is ejected after being deformed into a shape which facilitates the entrance of the intraocular lens 2 into the incision formed in the eyeball of the patient.

The distal end member 10a has what is called a bevel-cut shape, which is an obliquely cut shape, such that an upper region of the nozzle body 10 extends more toward a front side than a lower region of the nozzle body 10. The bevel-cut shape distal end member 10a may be formed by obliquely cutting the distal end member 10a so as to have a straight line shape as viewed from a lateral direction or may be formed by obliquely cutting the distal end member 10a so as to have an outwardly bulging shape or a curved surface shape.

A stage groove 12a having a width slightly larger than a diameter of the lens body 2a of the intraocular lens 2 is formed on the stage member 12. The size of the stage groove 12a in the longitudinal direction is set larger than the total size of the intraocular lens 2 including the support members 2b, 2b extending from both sides of the intraocular lens 2. A setting surface 12b is formed of a bottom surface of the stage groove 12a. The position of the setting surface 12b in a vertical direction is set higher than the height position of a bottom surface of the through-hole 10c formed in the nozzle body 10, and the setting surface 12b and the bottom surface of the through-hole 10c are connected to each other by a bottom member inclined surface 10d.

The stage member 12 and the stage lid member 13 are integrally formed with each other. The size of the stage lid member 13 in the longitudinal direction is set substantially equal to the size of the stage member 12 in the longitudinal direction. The stage lid member 13 is connected to the stage member 12 by a thin-plate-like connecting member 14 which is formed in an extending manner toward the stage lid member 13 from a side surface of the stage member 12. The connecting member 14 is formed in a bendable manner at a center portion thereof, and the stage lid member 13 overlaps with the stage member 12 from above by bending the connecting member 14 so that the stage lid member 13 is closed.

In the stage lid member 13, ribs 13a and a rib 13b for reinforcing the stage lid member 13 and for stabilizing the position of the intraocular lens 2 are formed on the surface of the stage lid member 13 which faces the setting surface 12b in a lid closed state. Guide projections 13c are formed on the stage lid member 13 as an upper guide for the plunger 30. Further, the insertion hole 13d is formed in the stage lid member 13 and the insertion hole 13d is used for providing viscoelastic material for the intraocular lens 2 with the stage lid member 13 closed. The viscoelastic material is an example of a lubricant for facilitating the move of the intraocular lens to the distal end member 10a of the nozzle body 10. Hyaluronic acid is commonly used as the viscoelastic material.

Figure 4A:
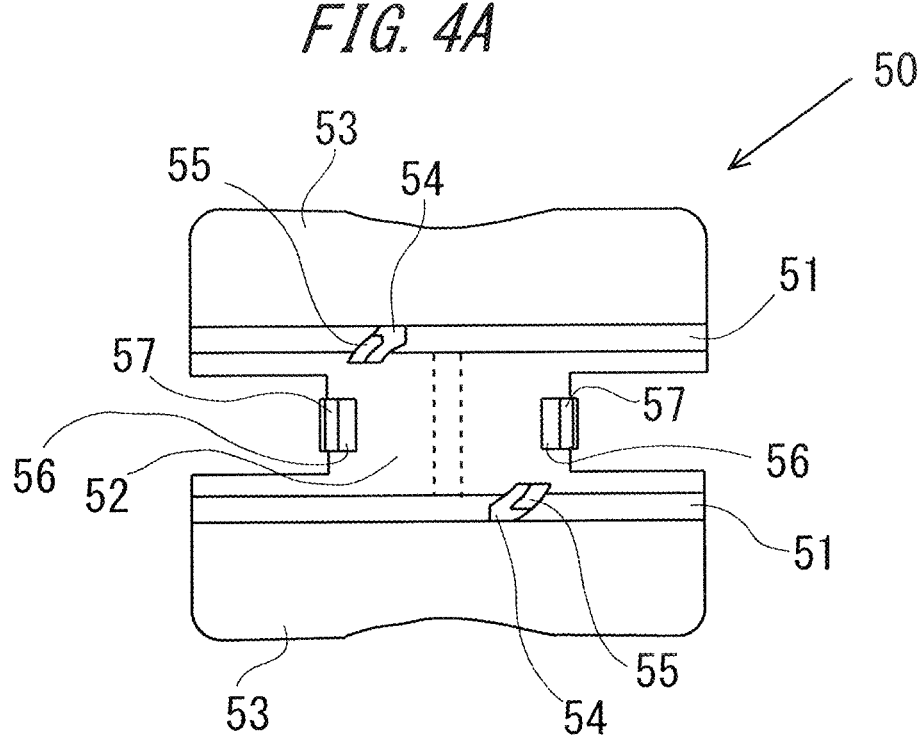
FIG. 4A A diagram illustrating the schematic configuration of a positioning member according to one embodiment.
Figure 4B:
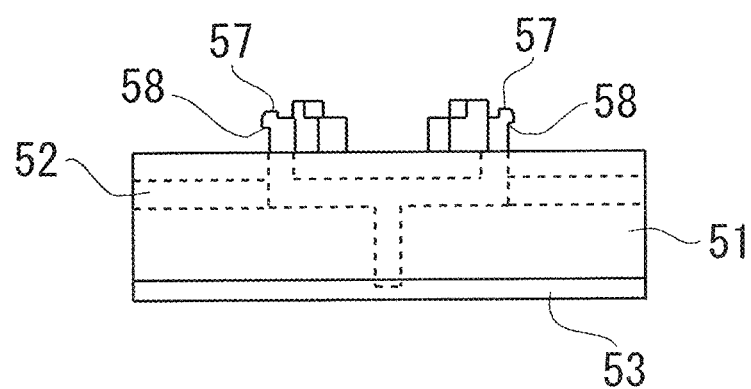
FIG. 4B A diagram illustrating the schematic configuration of the positioning member in FIG. 4B according to one embodiment.

The positioning member 50 is detachably mounted on a lower side of the setting surface 12b of the stage member 12. FIG. 4A and FIG. 4B illustrate a schematic configuration of the positioning member 50. FIG. 4A is a plan view of the positioning member 50, and FIG. 4B is a left side view of the positioning member 50. The positioning member 50 is formed as a body separate from the nozzle body 10, and is configured such that a pair of side wall members 51 is connected to each other by a connecting member 52. Holding members 53 which extend and expand outwardly are formed on lower ends of the side wall members 51.

A pair of the first placing members 54 which has an arcuate shape as viewed from above and projects upward is formed on the upper end members of the respective side wall members 51. The first positioning members 55 are formed on the outer peripheral sides of the upper end surfaces of the first placing members 54 in a projecting manner. The distance between the inner arcuate peripheral sides of the first positioning members 55 is set slightly larger than the diameter of the lens body 2a of the intraocular lens 2.

A pair of second placing members 56 which has a rectangular shape as viewed from above and projects upward is formed on both ends of the connecting member 52 in the longitudinal direction. The height of the upper surfaces of the second placing members 56 is set substantially equal to the height of the upper surfaces of the first placing members 54. Second positioning members 57 which project further upward are formed on the outer portions of the upper surfaces of the second placing members 56 such that the second positioning members 57 extend over the whole regions of the second placing members 56 in the lateral direction. The distance between the inner sides of the second positioning members 57 is set slightly larger than the diameter size of the lens body 2a of the intraocular lens 2. In addition, engaging pawls 58 which project slightly in the longitudinal direction respectively are formed on the upper end members of the second placing members 56 respectively over the whole region of the upper end members in the lateral direction.

The above-mentioned positioning member 50 is assembled to the nozzle body 10 from below the setting surface 12b of the nozzle body 10. The setting surface through-holes 12c which penetrate the setting surface 12b in the thickness direction are formed in the setting surface 12b of the nozzle body 10. The profiles of the setting surface through-holes 12c have a shape slightly larger than and substantially similar to the shape of the first placing members 54 and the shape of the second placing members 56 of the positioning member 50 as viewed from above. When the positioning member 50 is mounted on the nozzle body 10, the first placing members 54 and the second placing members 56 are inserted into the setting surface through-holes 12c from below the setting surface 12b, and project upward from the setting surface 12b.

At this stage of the operation, the engaging pawls 58 respectively formed on the second positioning members 57 project from the setting surface 12b through the setting surface through-holes 12c, and are engaged with the upper surface of the setting surface 12b. With such a configuration, the positioning member 50 is assembled to the nozzle body 10 from below, and the first placing members 54 and the second placing members 56 are fixed to the setting surface 12b in a state where the first placing members 54 and the second placing members 56 project from the setting surface 12b. Then, in setting the intraocular lens 2 on the setting surface 12b, the bottom surface of the outer peripheral portion of the lens body 2a is placed on the upper surfaces of the first placing members 54 and the upper surfaces of the second placing members 56. The position of the lens body 2a in the horizontal direction (the direction horizontal to the setting surface 12b) is restricted by the first positioning members 55 and the second positioning members 57.

In inserting the intraocular lens 2 into the eyeball using the insertion apparatus 1, firstly, hyaluronic acid which is a lubricant necessary for the intraocular lens 2 to move in the nozzle 10 is injected into a position where the hyaluronic acid is necessary by inserting a needle of a syringe through the distal end member 10a of the nozzle body 10 or the insertion hole 13d. When the necessary amount of hyaluronic acid is injected, the positioning member 50 is detached from the nozzle body 10. With such an operation, the first placing members 54 and the second placing members 56 which support the lens body 2a of the intraocular lens 2 are retracted from the setting surface 12b, and the intraocular lens 2 is placed on the setting surface 12b in a movable manner. And the user pushes the plunger 30 to move the intraocular lens to a predetermined position.

Next, the user inserts the distal end member 10a of the nozzle body 10 through the incision produced in the ophthalmic tissue. With this operation, the positional relationship between the distal end member 10a and the incision is determined. After the distal end member 10a of the nozzle body 10 is positioned with respect to the incision, the user pushes the pushing plate member 33 of the plunger 30 toward the distal end of the nozzle body 10. As a result, the distal end of the operating member 31 of the plunger 30 is positioned behind the lens body 2a of the intraocular lens 2 set on the setting surface 12b, and the intraocular lens 2 is guided toward the distal end member 10a by the plunger 30.

FIG. 5A and FIG. 5B illustrate the schematic configuration of the plunger 30. A longitudinal length of the plunger 30 is set slightly larger than that of the nozzle body 10. The plunger 30 is formed of: an operating member 31 which is disposed on a distal end side and basically has a columnar shape; and an insertion member 32 which is disposed on a rear end side and basically has a rectangular rod shape. The operating member 31 is configured to include a columnar member 31a having a columnar shape and thin-plate-shaped flat members 31b expanding in the lateral direction from the columnar member 31a.

A notch member 31c is formed on the distal end portion of the operating member 31. As illustrated in FIG. 5A, the notch member 31c is formed on the operating member 31 in a groove shape such that the notch member 31c opens upward and penetrates the operating member 31 in a lateral direction. As can be understood from FIG. 5B, a groove wall disposed on the distal end side of the notch member 31c is formed of an inclined surface which extends upward as the inclined surface extends toward the distal end side of the operating member 31. On the other hand, the insertion member 32 has an approximately H-shaped cross section as a whole, and the size of the insertion member 32 in the lateral direction and the size of the insertion member 32 in the vertical direction are set slightly smaller than those of the through-hole 10c formed in the nozzle body 10. In addition, a disc-shaped pushing plate member 33 which expands in the vertical direction as well as in the lateral direction is formed on a rear end of the insertion member 32.

A pawl member 32a which projects toward the upper side of the insertion member 32 and is vertically movable due to elasticity of the material of the plunger 30 is formed on a portion of the insertion member 32 on the distal end side from the center in the longitudinal direction. When the plunger 30 is inserted into the nozzle body 10, an engaging hole 10e illustrated in FIG. 3 which is formed in the upper surface of the nozzle body 10 in the thickness direction and the pawl member 32a are engaged with each other. With such engagement, the relative position between the nozzle body 10 and the plunger 30 in the initial state is determined. The position where the pawl member 32a is formed and the position where the engaging hole 10e is formed are set such that, in an engaging state, the distal end of the operating member 31 is positioned behind the lens body 2a of the intraocular lens 2 set on the stage member 12, and the support members 2b on the rear side of the lens body 2a can be supported by the notch member 31c from below. Further, a concave member 34 is formed in the vicinity of the rear end of the insertion member 32. Since the user can hold the concave member 34 to push the plunger 30, the fine operation of the plunger 30 for injecting the intraocular lens 2 by the user can be achieved.

Before the intraocular lens 2 is accommodated in the insertion apparatus 1 having the above-mentioned configuration, the plunger 30 is arranged at an initial position in a state where the plunger 30 is inserted into the nozzle body 10. As described previously, the positioning member 50 is attached to the nozzle body 10 from below the setting surface 12b. With such a configuration, the first placing members 54 and the second placing members 56 of the positioning member 50 are held in a projecting manner from the setting surface 12b.

Next, the lens body 2a of the intraocular lens 2 is placed and positioned on the upper surfaces of the first placing members 54 and the upper surfaces of the second placing members 56 in a state where the support members 2b are directed in the longitudinal direction of the nozzle body 10.

In such a state, a part of the support member 2*b* on the rear side of the intraocular lens 2 is tucked by the groove walls of the notch member 31*c* of the plunger 30 and is supported by the bottom surface of the notch member 31*c* of the plunger 30.

Figure 6:
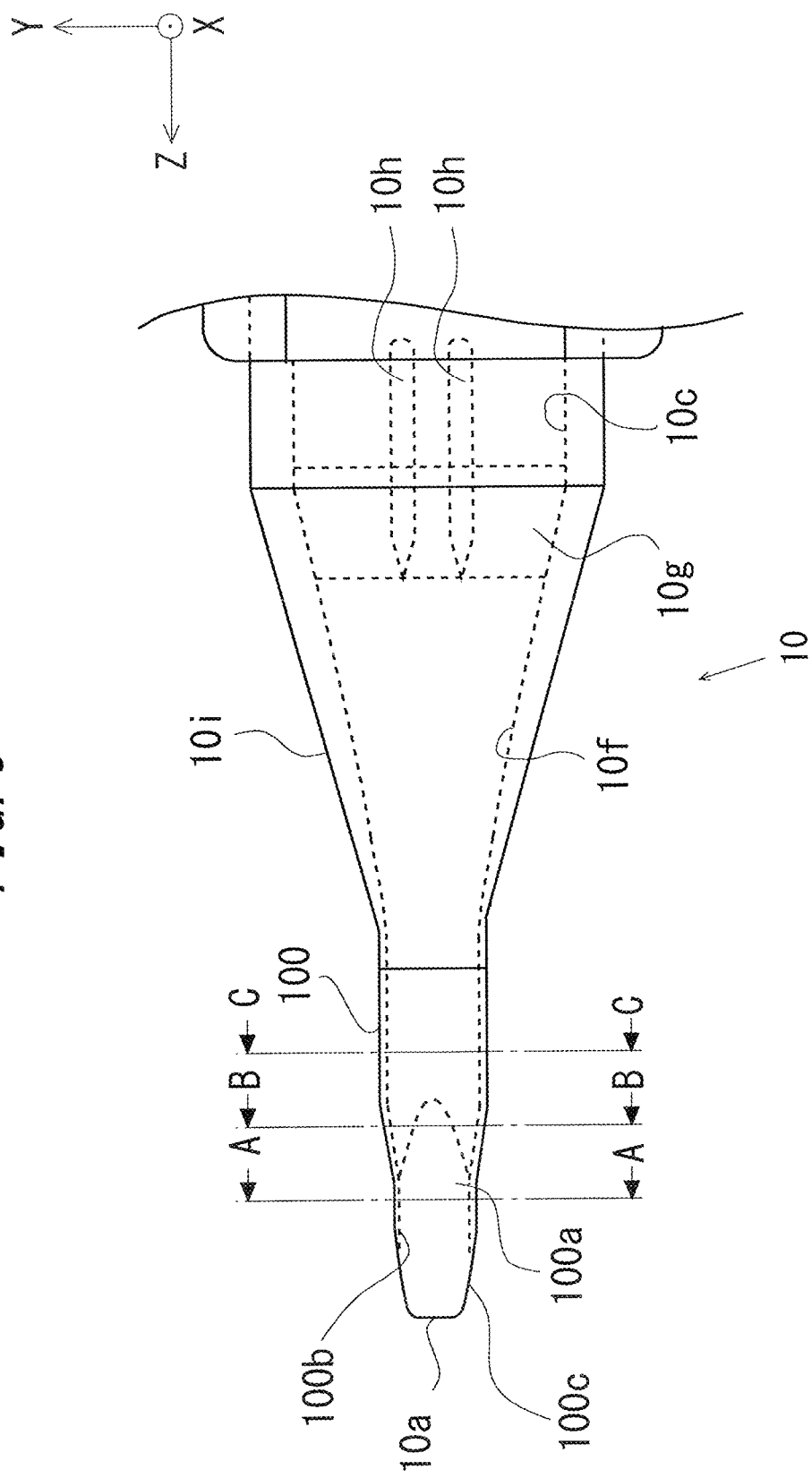
FIG. 6 A diagram illustrating the schematic configuration of the nozzle body and the distal end member of the intraocular lens insertion apparatus according to one embodiment.

Next, the configurations of the parts around the distal end member 10*a* of the nozzle body 10 are described below. FIG. 6 is a plan view illustrating the details around the insertion tube 100 of the nozzle body 10. The outer shape of the nozzle body 10 is generally a shape tapering toward the distal end member 10*a*. A shrinking member 10*f* the cross section of which is decreasing toward the distal end member 10*a* is formed for the through-hole 10*c*. Since the widths of the bottom surface and the upper surface of the shrinking member 10*f* decrease toward the distal end member 10*a*, the cross section of the shrinking member 10*f* also decreases. Thus, the intraocular lens is folded when the insertion apparatus 1 is used to push the intraocular lens through the shrinking member 10*f*. The thickness and the shape of the wall of the shrinking member 10*f* are configured to achieve the intraocular lens to be convex upward and to prevent the intraocular lens from being convex downward in the shrinking member 10*f*. Since it is not essential to configure the shrinking member 10*f* to achieve the intraocular lens to be convex upward, the shrinking member 10*f* can be allowed to be configured to achieve the intraocular lens to be convex downward due to other reasons. In any case, the thickness and the shape of the wall of the shrinking member 10*f* should be configured to achieve the folding of the intraocular lens as designed when the insertion apparatus 1 is used. It is noted that an inclined surface 10*g* is formed on the bottom surface at the rear end portion of the shrinking member 10*f* so that the bottom surface inclines toward the distal end member 10*a*. An uneven surface is produced by the inclined surface 10*g*.

A pair of introducing projections 10*h* which are directed in the Z-axis direction of the nozzle body 10 and between which the center of the nozzle body 10 resides is formed near the shrinking member 10*f* on the bottom surface of the through-hole 10*c*. The introducing projections 10*h* are provided in the longitudinal direction of the nozzle body 10 on the inclined surface 10*g* and the introducing projections 10*h* are formed to be in parallel and to slightly project from the bottom surface of the shrinking member 10*f* on the rear end side. It is noted that the height of the introducing projections 10*h* formed on the inclined surface 10*g* gradually increases to become even with the height of the distal end member 10*a* at the distal end of the inclined surface 10*g*. In addition, the distance between the introducing projections 10*h* is slightly larger than the width of the operating member 31 of the plunger 30.

Further, the through-hole 10*c* of the insertion tube 100 is formed to extend almost linearly with an approximately-constant cross section. In addition, the through-hole 10*c* of the insertion tube 100 includes a distal end opening member 100*a*. It is noted that the distal end opening member 100*a* is an example of an opening member. Further, the distal end opening member 100*a* includes a distal end area 100*b* provided on the side of the distal end member 10*a*. Moreover, a plate-like projecting member 100*c* is provided in the distal end area 100*b*. The projecting member 100*c* is a member which extends in the direction of the pushing direction of the plunger 30 in the nozzle body 10, that is the direction toward which the intraocular lens is moved and the Z-axis direction as indicated in FIG. 7.

Figure 7:
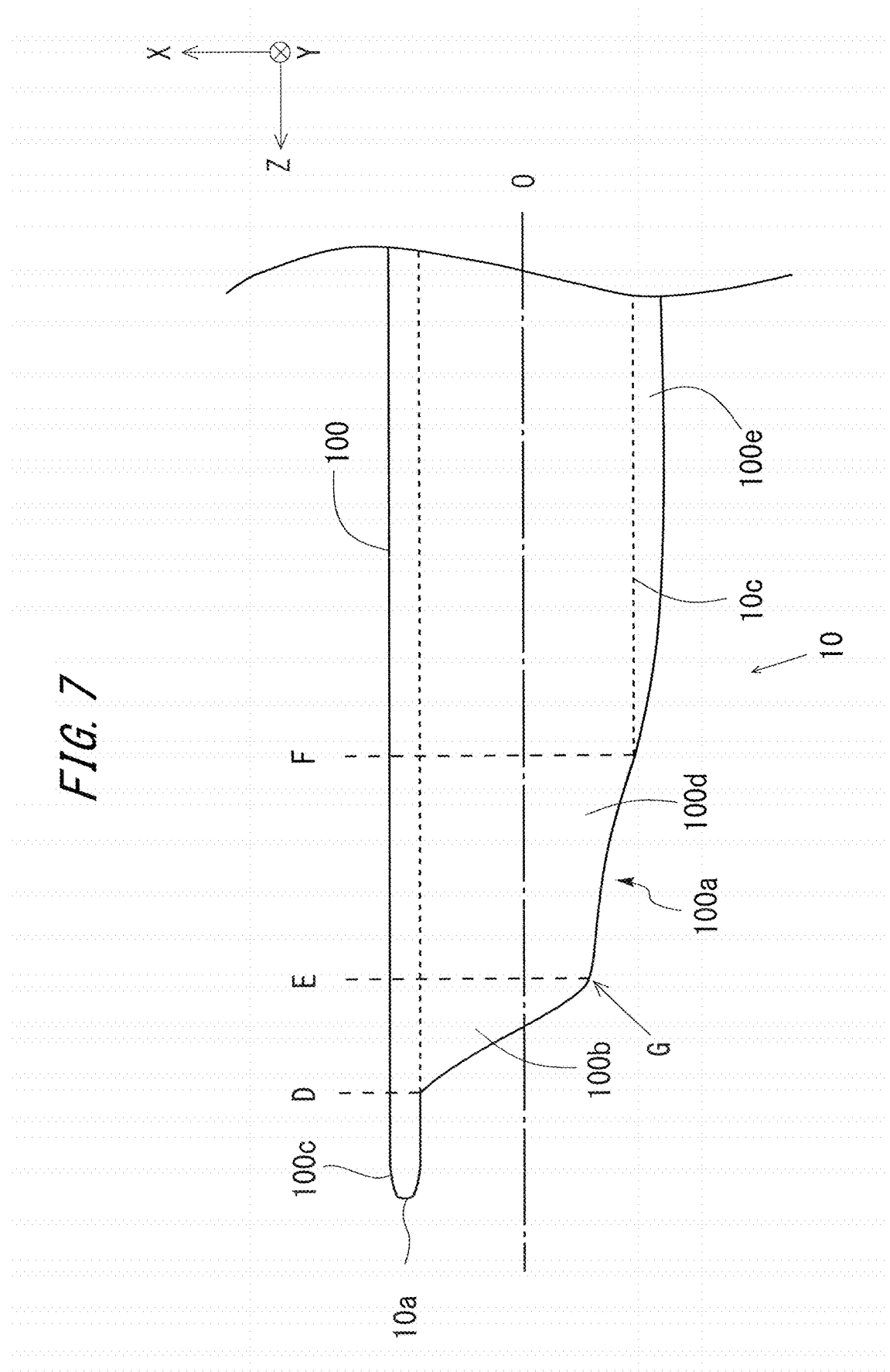
FIG. 7 A diagram illustrating a side view of the distal end member of the intraocular lens insertion apparatus according to one embodiment.

As illustrated in FIG. 7, the distal end opening member 100*a* is formed by beveling the insertion tube 100 so that the cutting surface transits toward the negative side of the X-axis as the cutting surface transits toward the negative side of the Z-axis. That is, the upper end portion of the insertion tube 100 projects further forward than the lower end portion of the insertion tube 100. In addition, the distal end opening member 100*a* has a folding point G at which the curvature of the contour of the distal end opening member 100*a* changes significantly in the lateral view. It is assumed here in the distal end opening member 100*a* that the area on the side of the distal end member 10*a* as seen from the folding point G is the distal end area 100*b* and the area on the side of the rear end member 10*b* as seen from the folding point G is the rear end area 100*d*.

Moreover, the central axis O is set in the direction parallel with the Z-axis of the nozzle body 10. The distal end opening member 100*a* includes the distal end area 100*b* and the rear end area 100*d*. The opening end surface of the distal end opening member 100*a* is an inclined surface which is inclined to the surface perpendicular to the central axis O. In addition, the inclination angle to the plane perpendicular to the central axis O regarding the inclined surface in the distal end area 100*b* is configured to be smaller than the inclination angle to the plane perpendicular to the central axis O regarding the inclined surface in the rear end area 100*d*. Therefore, the lateral wall in the distal end area 100*b* is formed to rise steeply in the X-axis direction in the lateral view of the distal end opening member 100*a*. Then, the rear end area 100*d* connects the lateral wall in the distal end area 100*b* to the body member 100*e* with its height gradually increased in the X-axis direction. The lateral wall in the distal end area 100*b* gradually increases its height in the X-axis direction to connect to the body member 100*e*. The lateral wall in the distal end area 100*b* is a member extending in the direction of the optical axis (the X-axis direction in FIG. 7) of the intraocular lens 2 positioned on the stage member 12. The direction (the X-axis direction in FIG. 7) in which the lateral wall in the distal end area 100*b* extends is perpendicular to the direction (the Z-axis direction in FIG. 7) in which the plunger 30 is pushed in the nozzle body 10, in which the intraocular lens 2 is moved in the nozzle body 10 and in which the projecting member 100*c* extends in the nozzle body 10.

Additionally, the outer shape of the distal end opening member 100*a* is a shape tapering toward the distal end member 10*a* as illustrated in FIG. 6. It is noted that although the outer shape of the distal end opening member 100*a* in the distal end area 100*b* is not a tapered shape, the outer shape of the distal end opening member 100*a* over the entire length from the rear end area 100*d* to the distal end area 100*b* can be configured to be a tapered shape. Since the outer shape of the distal end opening member 100*a* is configured to be such a tapered shape, it is easier to insert the distal end opening member 100*a* through the small incision compared to conventional distal end opening members.

Figure 8:
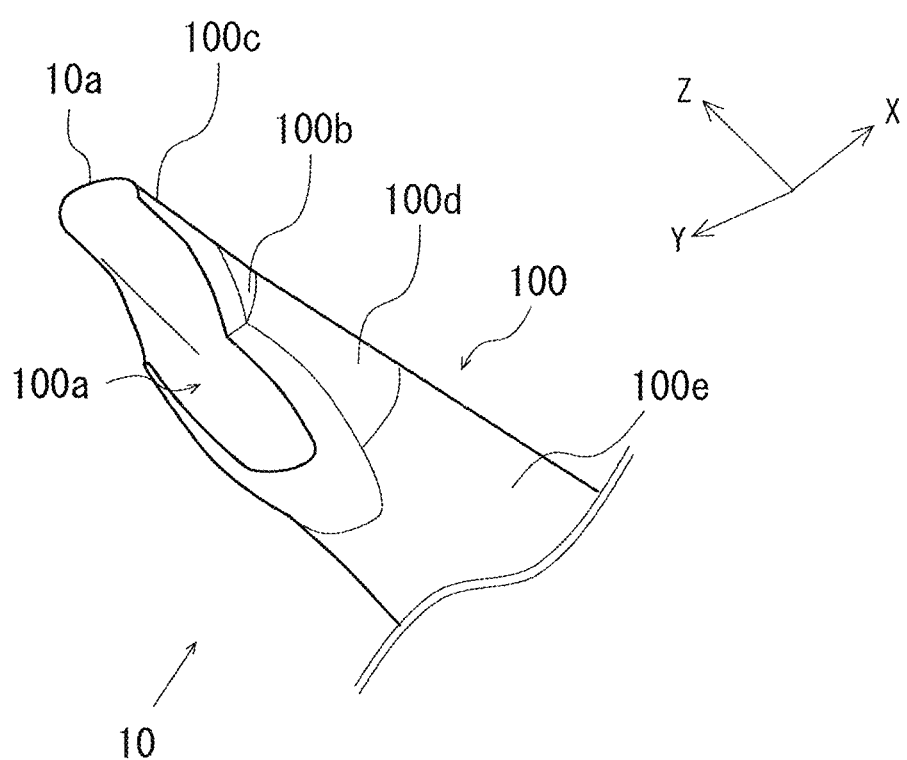
FIG. 8 A diagram illustrating a perspective view of the distal end member of the intraocular lens insertion apparatus according to one embodiment.

As illustrated in FIG. 6, the nozzle body 10 includes a tapered member 10*i* which has a shape tapering toward the distal end member 10*a*. In addition, as illustrated in FIG. 8, the distal end opening member 100*a* of the insertion tube 100 of the nozzle body 10 opens toward the negative side of the X-axis. Further, as illustrated in FIGS. 7 and 8, the insertion tube 100 includes a body member 100*e*, the rear end area 100*d*, the distal end area 100*b* and the projecting member 100*c* aligned in the direction from the rear end member 10*b* to the distal end member 10*a* of the nozzle body 10. It is noted in FIG. 7 that when the insertion tube 100 is divided by planes perpendicular to the Z-axis, the portion from the plane F to the rear end member 10*b* corresponds to as the body member 100e, the portion between the plane E and the plane F corresponds to the rear end area 100d, the portion between the plane D and the plane E corresponds to the distal end area 100b and the portion from the plane D to the distal end member 10a corresponds to the projecting member 100c.

The body member 100e is a member the shape of which is hollow and tube-like. As illustrated in FIG. 7, the thickness of the body member 100e on the bottom side gradually decreases toward the distal end member 10a. The surface of the body member 100e and the surface of the rear end area 100d are smoothly connected with each other at the position indicated by the plane F. The rear end area 100d tapers toward the distal end member 10a. That is, the diameter of the rear end area 100d decreases toward the distal end member 10a so that the cross-section of the distal end opening member 100a in the X-Y plane decreases. Further, the height of the lateral wall of the rear end area 100d in the X-axis direction gradually decreases as illustrated in FIGS. 7 and 8. Therefore, the surface of the rear end area 100d is smoothly connected with the surface of the body member 100e and the surface of the distal end area 100b.

The distal end area 100b includes an upper surface which is approximately parallel with the Y-Z plane, and a lateral wall which is approximately perpendicular to the upper surface and which is approximately parallel with the X-Z plane. The upper surface of the distal end area 100b is connected with the projecting member 100c on the side of the distal end member 10a. As illustrated in FIG. 7, the height of the lateral wall in the distal end area 100b in the X-axis direction steeply rises from the position indicated by the plane D to the position indicated by the plane E. Thus, since the lateral wall in the distal end area 100b is configured as such at the position immediately subsequent to the projecting member 100c, the movement of the intraocular lens can be stably maintained to guide the intraocular lens into the crystalline capsule. In addition, as illustrated in FIGS. 7 and 8, the projecting member 100c is a tabular member the upper surface of which projects toward the distal end member 10a and is approximately parallel with the Y-Z plane in the distal end area 100b.

Figure 9A:
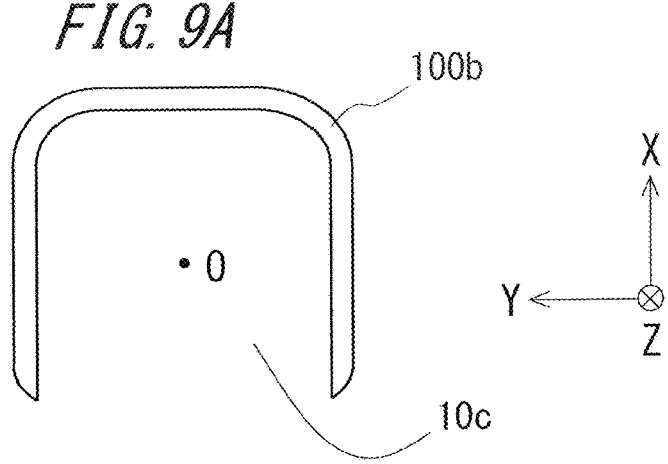
FIG. 9A A diagram illustrating a cross-sectional view of an insertion tube of the intraocular lens insertion apparatus according to one embodiment.
Figure 9B:
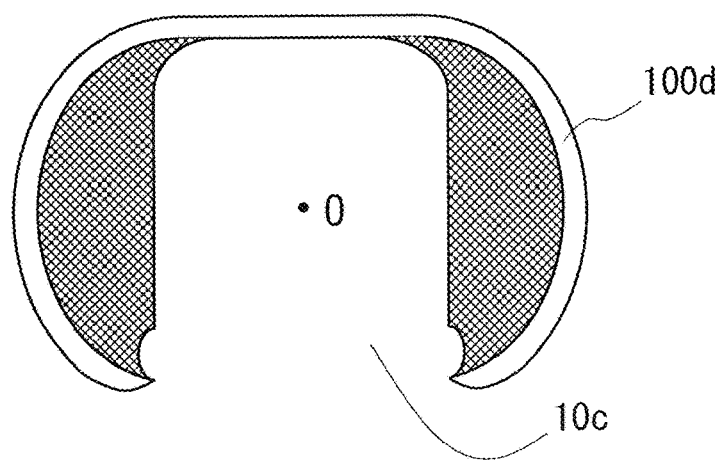
FIG. 9B A diagram illustrating another cross-sectional view of an insertion tube of the intraocular lens insertion apparatus according to one embodiment.
Figure 9C:
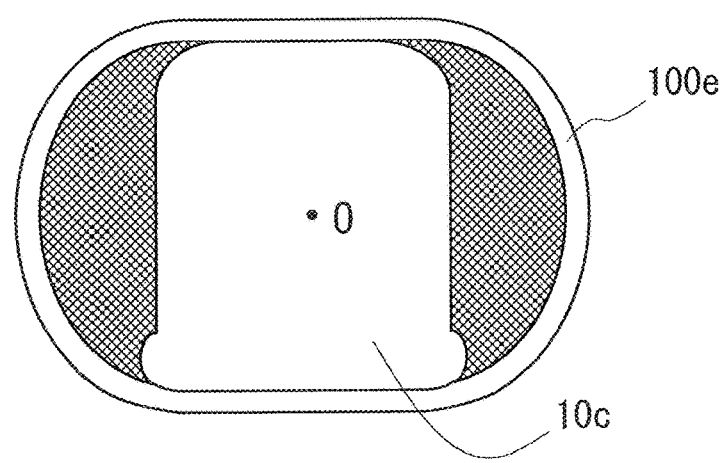
FIG. 9C A diagram illustrating still another cross-sectional view of an insertion tube of the intraocular lens insertion apparatus according to one embodiment.

FIG. 9 is a diagram illustrating the cross-sections at three different positions of the insertion tube 100 of the nozzle body 10. Specifically, FIG. 9A illustrates a cross-section indicated by the line A-A in FIG. 6, FIG. 9B illustrates a cross-section indicated by the line B-B in FIG. 6 and FIG. 9C illustrates a cross-section indicated by the line C-C in FIG. 6. In addition, the cross-section in FIGS. 9A to 9C illustrate the insertion tube 100 as seen from the negative side to the positive side in the Z-axis direction, that is as seen from the rear end member 10b to the distal end member 10a in the nozzle body 10.

As illustrated in FIG. 9A, the distal end area 100b provided on the side of the distal end of the distal end opening member 100a is configured so that a pair of lateral walls which are approximately parallel with the X-Z plane are approximately perpendicular to the upper surface which is approximately parallel with the Y-Z plane and the pair of lateral walls is smoothly connected with the upper surface. In addition, as illustrated in FIG. 9B, the shape of the cross-section of the rear end area 100d is a shape obtained by modifying the tabular lateral wall in the distal end area 100b to a curved lateral wall. Further, as illustrated in FIG. 9C, the shape of the cross-section of the body member 100e is a shape in which the lower surface facing the upper surface between which the central axis O resides is provided in addition to the upper surface and the lateral walls in the rear end area 100d. Moreover, the through-hole 10c is surrounded by the upper surface, the lower surface and the pair of lateral walls.

Since the insertion tube 100 is configured as described above, the intraocular lens 2 can be moved through the tapered member 10i and the body member 100e of the insertion tube 100 to reach the distal end opening member 100a by the operation of pushing the plunger 30. In addition, the intraocular lens 2 is moved to the rear end area 100d, and moved to the distal end area 100b with the intraocular lens 2 being folded, and moved to the crystalline capsule with the shape of the intraocular lens 2 being maintained by the lateral walls of the distal end area 100b. As a result, when the intraocular lens 2 is guided into the crystalline capsule, the intraocular lens 2 moved to the distal end opening member 100a can be prevented from being ejected to the outside of the eyeball.

Since the projecting member 100c is provided for the distal end of the insertion tube 100, this configuration improves the insertion of the insertion tube 100 through a small incision into the eyeball. In addition, since the distal end area 100b and the rear end area 100d are provided subsequent to the projecting member 100c, the intraocular lens 2 can be stably guided into the crystalline capsule after a predetermined length of the insertion tube 100 is inserted into the eyeball. Further, when the intraocular lens 2 is guided as described above, the intraocular lens 2 can be prevented from being ejected to the outside of the eyeball unexpectedly for the user.

In an example of the intraocular lens insertion apparatus 1 according to the present embodiment, the length of the projecting member 100c in the Z-axis direction is approximately 1.0 mm, the width of the projecting member 100c in the Y-axis direction is approximately from 1.1 mm to 1.6 mm, the length of the distal end area 100b in the Z-axis direction is approximately 1.0 mm, the length of the rear end area 100d in the Z-axis direction is approximately 1.5 mm and the width of the insertion tube 100 in the Y-axis direction is approximately from 1.6 mm to 2.4 mm. With such configurations, the intraocular lens insertion apparatus can be inserted through a small incision more easily than conventional intraocular lens insertion apparatuses and can guide the intraocular lens into the crystalline capsule more stably than the conventional intraocular lens insertion apparatuses.

Next, an example in which the intraocular lens insertion apparatus 1 according to the present embodiment is inserted into a cornea of a patient is described below. It is assumed in the present embodiment that the intraocular lens insertion apparatus 1 is inserted in the direction perpendicular to the ocular axis of the eyeball through an incision produced in the cornea.

Figure 10:
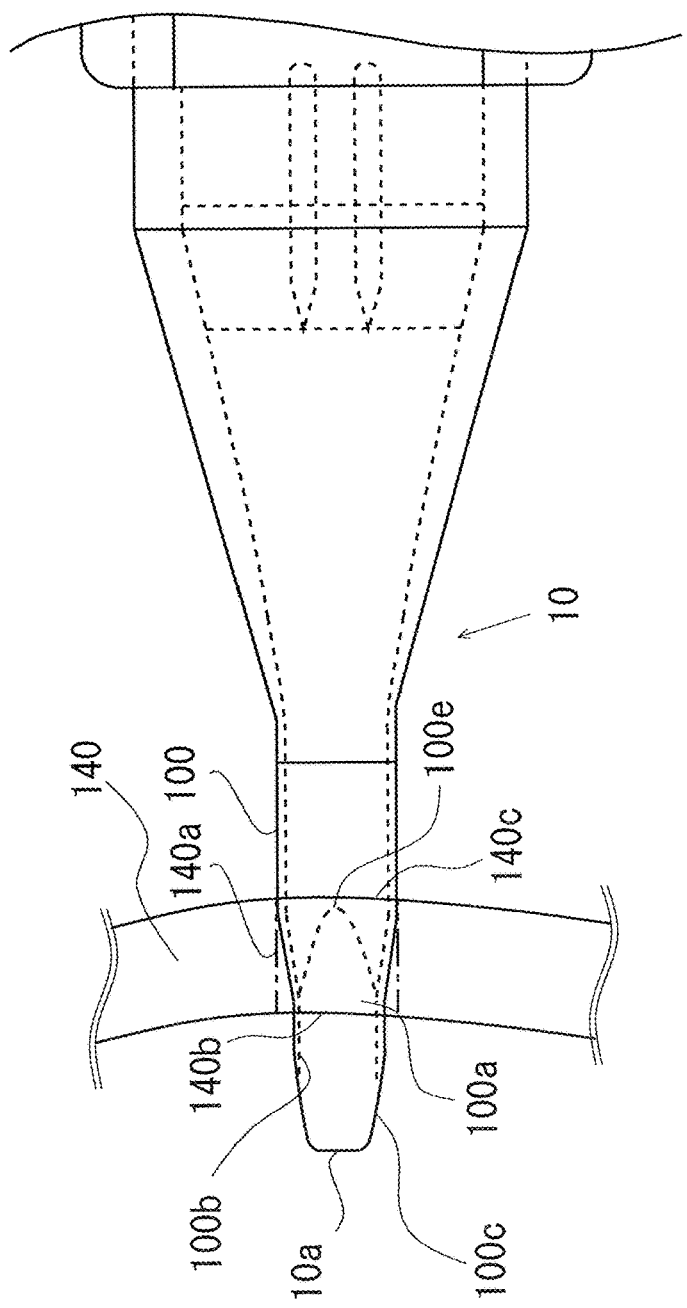
FIG. 10 A diagram illustrating a state in which the intraocular lens insertion apparatus is inserted through an incision in one embodiment.

FIG. 10 is a schematic diagram illustrating that the intraocular lens insertion apparatus 1 is inserted through the incision 140a in the cornea 140. In the example in FIG. 10, the distal end member 10a of the nozzle body 10 of the intraocular lens insertion apparatus 1 projects into the eyeball from the cornea through the external flap 140c and internal flap 140b of the incision 140a. In addition, the body member 100e of the distal end opening member 100a of the nozzle body 10 on the negative side of the Z-axis is inside the cornea 140 with respect to the external flap 140c, that is the entire distal end opening member 100a is inside the cornea 140 with respect to the external flap 140c. Therefore, since the distal end opening member 100a does not exist outside the external flap 140c of the incision 140a, the abnormal behavior of the intraocular lens does not occur when the intraocular lens is ejected through the distal end opening member 100a.

Further, the shape of the distal end member 10a of the nozzle body 10 which projects toward the inside of the eyeball from the internal flap 140b of the incision 140a is approximately a rectangle in the top view viewing in the X-axis direction from the positive side to the negative side. Namely, the direction of the optical axis of the intraocular lens 2 set to the intraocular lens insertion apparatus 1 is the X-axis direction and the length of the distal end member 10a which projects from the internal flap 140b of the incision 140a in the insertion direction (the Z-axis direction) of the intraocular lens insertion apparatus 1 is longer than the length of that in the direction (the Y-axis direction) perpendicular to the insertion direction when the distal end member 10a is viewed in the X-axis direction in the top view.

Thus, the intraocular lens insertion apparatus 1 according to the present embodiment can achieve an appropriate insertion length from incision 140a into the eyeball. Namely, the length of the distal end opening member 100a in the longitudinal direction (the Z-axis direction) in the top view and the dimensions of the distal end opening member 100a are configured so that the shape of the distal end member 10a of the nozzle body 10 in the top view is a rectangle the long sides of which are parallel with the Z-axis when the entire distal end opening member 100a is inserted inside the external flap 140c of the cornea 140 through the incision 140a. Thus, the user can check the shape of the distal end member 10a of the nozzle body 10 in the top view which projects from the internal flap 140b of the incision 140a to determine whether the insertion length of the intraocular lens insertion apparatus 1 inserted into the eyeball through incision 140a is adequate, when the user insert the intraocular lens insertion apparatus 1 into the eyeball through the incision 140a produced in the cornea 140 of the patient.

Figure 11:
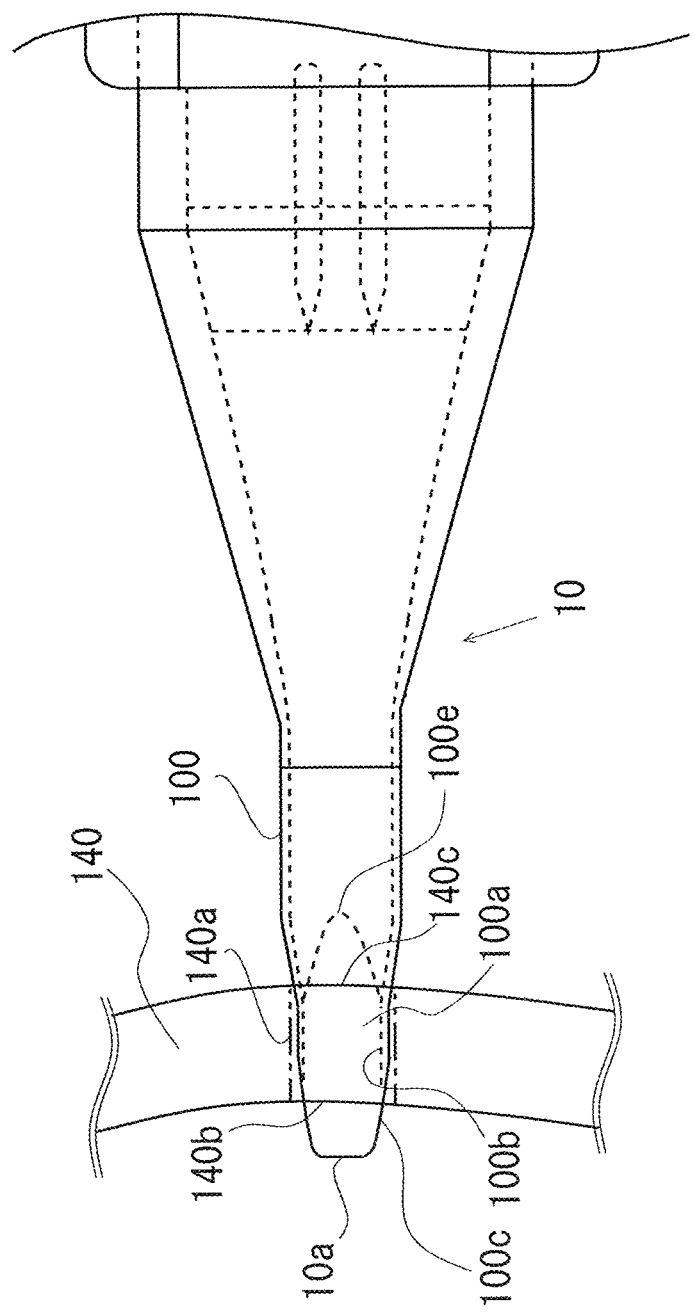
FIG. 11 A diagram illustrating another state in which the intraocular lens insertion apparatus is inserted through an incision in one embodiment.

FIG. 11 is a schematic diagram illustrating an example different from the example in FIG. 10 in which the intraocular lens insertion apparatus 1 is inserted through the incision 140a of the cornea 140. In the example illustrated in FIG. 11, the distal end member 10a of the nozzle body 10 of the intraocular lens insertion apparatus 1 projects from the cornea 140 through the external flap 140c and the internal flap 140b of the incision 140a. In addition, the body member 100e of the distal end opening member 100a on the negative side of the Z-axis is positioned outside the external flap 140c, that is outside the cornea 140. Therefore, since a part of the distal end opening member 100a is outside the external flap 140c of the incision 140a (on the negative side of Z-axis), an abnormal behavior of the intraocular lens may occur when the intraocular lens is ejected through the distal end opening member 100a.

In addition, the shape of the distal end member 10a of the nozzle body 10 in the top view which projects from the internal flap 140b of the incision 140a is approximately a square. Namely, the length of the distal end member 10a which projects from the internal flap 140b of the incision 140a in the insertion direction (the Z-axis direction) of the intraocular lens insertion apparatus 1 is approximately equal to the length of that in the direction (the Y-axis direction) perpendicular to the insertion direction when the distal end member 10a is viewed in the direction (the X-axis direction) of the optical axis of the intraocular lens 2 set to the intraocular lens insertion apparatus 1 in the top view.

Thus, when the intraocular lens insertion apparatus 1 according to the present embodiment cannot achieve an appropriate insertion length from incision into the eyeball, namely the abnormal behavior may occur because a part of the distal end opening member 100a is outside the external flap 140c of the incision 140a, the length of the distal end opening member 100a in the longitudinal direction (the Z-axis direction) in the top view and the dimensions of the distal end opening member 100a are configured so that the shape of the distal end member 10a of the nozzle body 10 in the top view is approximately a square. Since the distal end member 10a is configured as described above, the part of the distal end member 10a which projects from the internal flap 140b of the incision 140a can be used as indicating means.

Therefore, the user can check whether the shape of the distal end member 10a of the nozzle body 10 in the top view which projects from the internal flap 140b of the incision 140a is approximately a square to determine whether the insertion length of the intraocular lens insertion apparatus 1 inserted into the eyeball through incision 140a is adequate, when the user insert the intraocular lens insertion apparatus 1 into the eyeball through the incision 140a produced in the cornea 140 of the patient.

Thereafter, when the user determines that the insertion length of the intraocular lens insertion apparatus 1 inserted from the incision 140a is not adequate, the user pushes the intraocular lens insertion apparatus 1 toward the eyeball to achieve that the shape of the part of the intraocular lens insertion apparatus 1 in the top view which projects from the internal flap 140b of the incision 140a as illustrated in FIG. 10 is approximately a rectangle. As a result, the user can achieve an appropriate insertion length of the intraocular lens insertion apparatus 1 inserted through the incision 140a.

Although the present embodiment is described as above, the configurations and the processes of the information processing apparatus are not limited to those as described above and various variations may be made to the embodiment described herein within the technical scope of the above embodiment. Modifications of the above-mentioned embodiment are exemplified hereinafter. In the description made hereinafter, respective constitutional elements corresponding to the constitutional elements of the above-mentioned embodiment are given the same symbols, and the repeated description of the constitutional elements is omitted unless otherwise specified.

Figure 12:
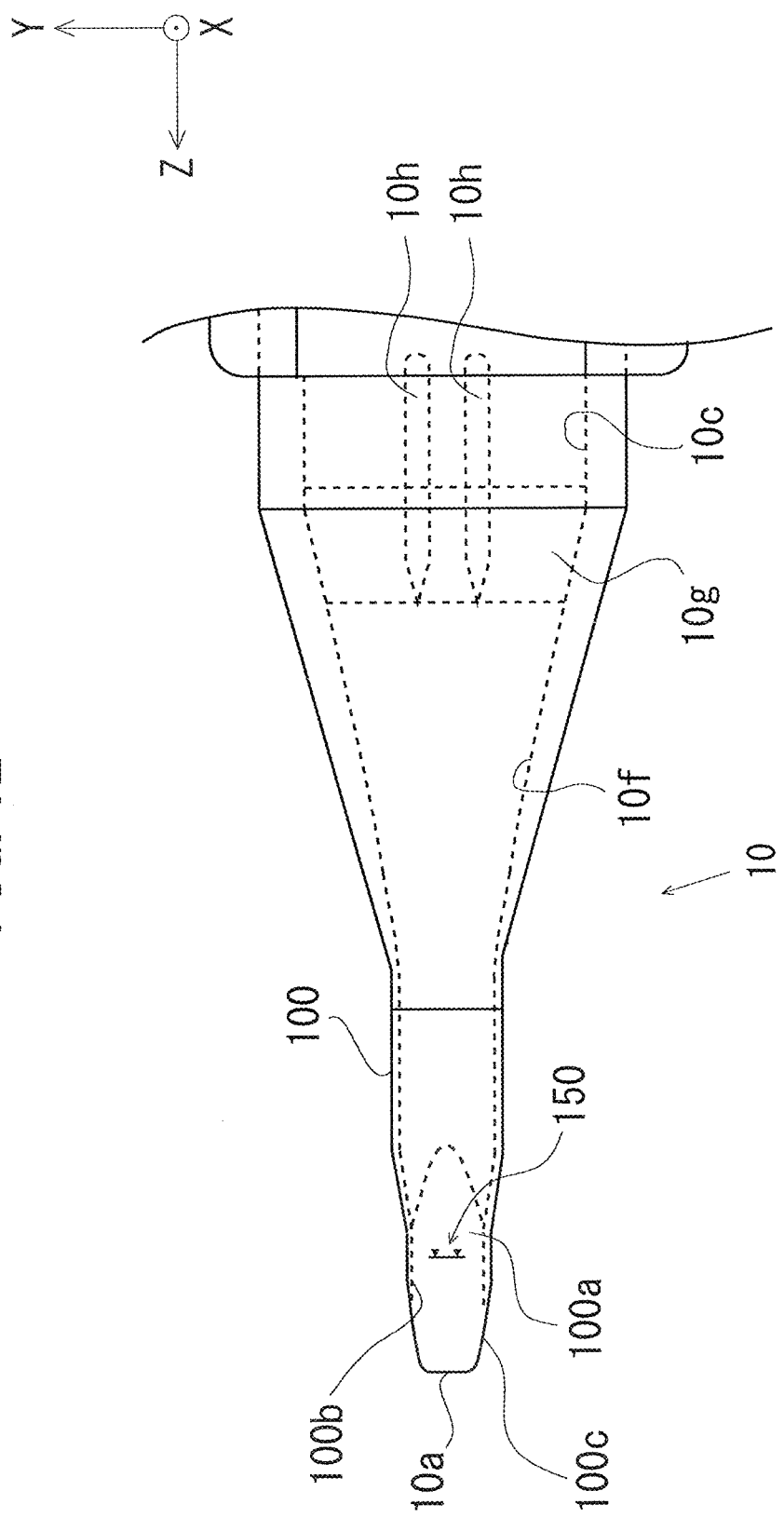
FIG. 12 A diagram illustrating the schematic configurations of the nozzle body and the distal end member of the intraocular lens insertion apparatus according to one embodiment.

FIG. 12 is a plan view illustrating the details of an insertion tube 100 of the nozzle body 10. In the present modification, an indicator 150 is provided on the distal end member 10a of the nozzle body 10 at a position at which the indicator 150 overlaps the distal end opening member 100a in the top view. It is noted that the indicator 150 is an example of an indicating means. As illustrated in FIG. 12, when the intraocular lens insertion apparatus 1 is inserted from the incision 140a, the position of the intraocular lens insertion apparatus 1 in the top view in the direction (the X-axis direction) of the optical axis of the intraocular lens 2 set in the intraocular lens insertion apparatus 1 is determined so that the indicator 150 overlaps the internal flap 140b of the incision 140a. Since the intraocular lens insertion apparatus 1 can be positioned as described above, a state in which an abnormal behavior of the intraocular lens does not occur can be achieved when the intraocular lens is ejected through the distal end opening member 100a.

Figure 13:
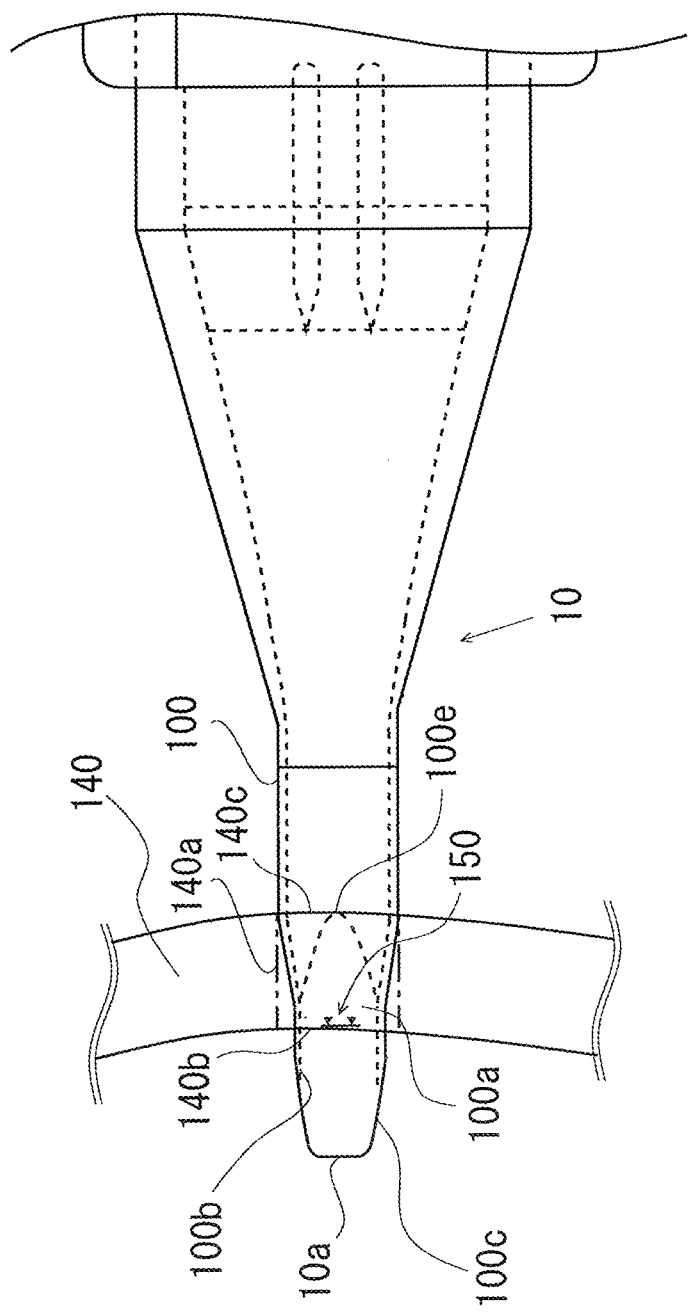
FIG. 13 A diagram illustrating still another state in which the intraocular lens insertion apparatus is inserted through an incision in one embodiment.

FIG. 13 is a schematic diagram illustrating that the intraocular lens insertion apparatus 1 is inserted through the incision 140a of the cornea 140 of the patient. In the example in FIG. 13, the distal end member 10a of the nozzle body 10 projects toward the eyeball from the cornea 140 through the external flap 140c and the internal flap 140b of the incision 140a. In addition, the intraocular lens insertion apparatus 1 is inserted into the eyeball through the incision 140a with the indicator 150 of the distal end member 10a of the intraocular lens insertion apparatus 1 overlapping the internal flap 140b of the cornea 140 in the top view of the distal end member 10a.

As illustrated in FIG. 13, the end member 100e which is provided on the negative side of the Z-axis of the distal end opening member 100a of the nozzle body 10 largely overlaps the external flap 140c of the incision 140a, that is the entire distal end opening member 100a is inside the cornea 140 with respect to the external flap 140c. Therefore, since the distal end opening member 100a is not positioned outside the external flap 140c of the incision 140a (on the negative side of the Z-axis), it can be assumed that an abnormal behavior of the intraocular lens does not occur when the intraocular lens is ejected through the distal end opening member 100a.

Thus, the user can control the insertion length of the intraocular lens insertion apparatus 1 inserted through the incision 140a by aligning the indicator 150 provided on the distal end member 10a of the nozzle body 10 with the internal flap 140b of the incision 140a in the top view of the distal end member 10a when the user inserts the intraocular lens insertion apparatus 1 into the eyeball through the incision 140a of the cornea 140.

Figure 14:
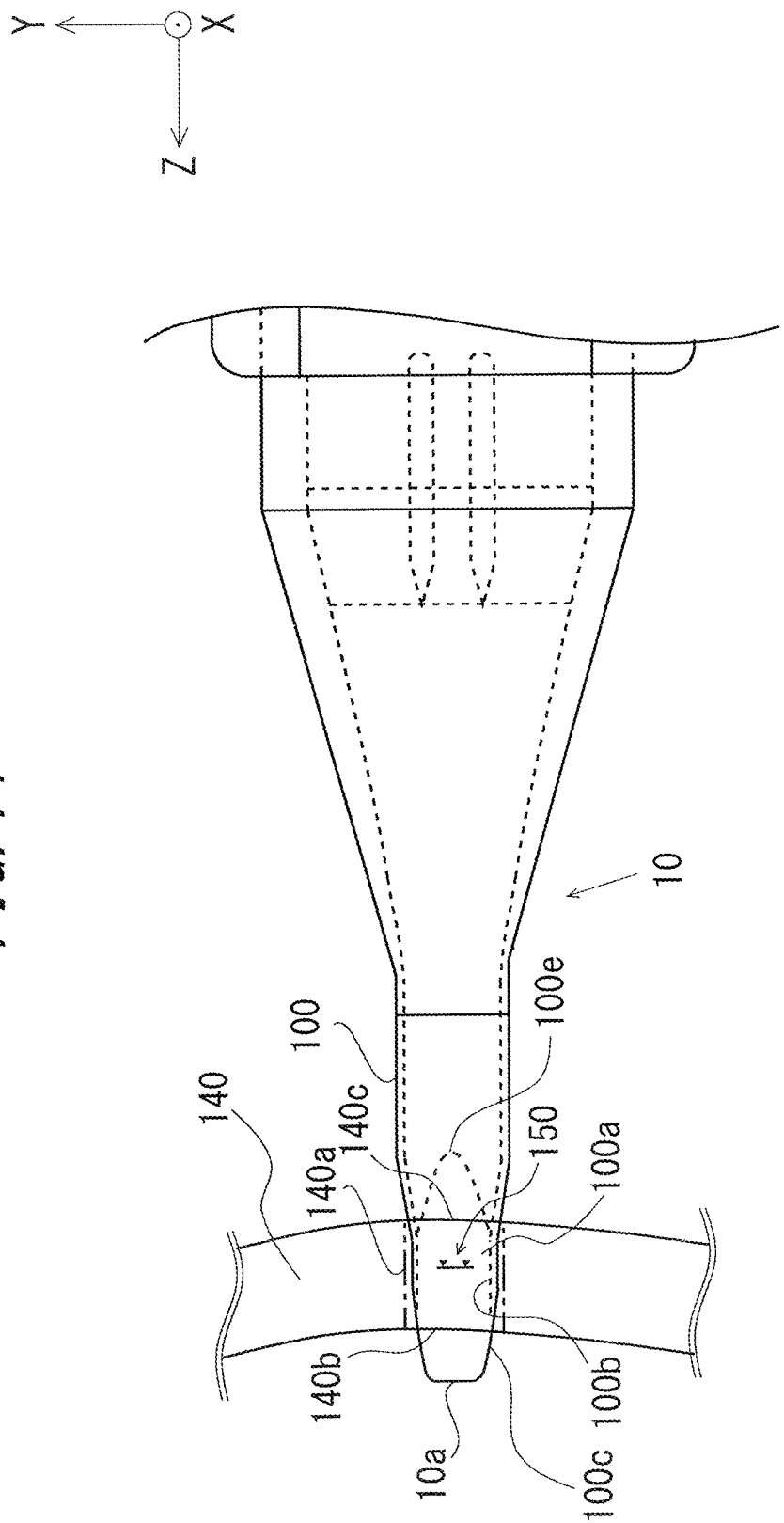
FIG. 14 A diagram illustrating yet another state in which the intraocular lens insertion apparatus is inserted through an incision in one embodiment.

FIG. 14 is a schematic diagram illustrating an example different from the example in FIG. 13 in which the intraocular lens insertion apparatus 1 is inserted through the incision 140a of the cornea 140. In the example in FIG. 14, the distal end member 10a of the nozzle body 10 of the intraocular lens insertion apparatus 1 projects from the cornea 140 through the external flap 140c and the internal flap 140b of the incision 140a. In contrast to the example in FIG. 13, the indicator 150 provided on the distal end member 10a of the nozzle body 10 is positioned outside the internal flap 140b of the incision 140a (on the side of the external flap 140c) in the top view of the distal end member 10a of the intraocular lens insertion apparatus 1. In addition, the body member 100e which is provided on the negative side of the Z-axis of the distal end opening member 100a of the nozzle body 10 is positioned outside the external flap 140c of the incision 140a (on the negative side of the Z-axis). Therefore, since a part of the distal end opening member 100a is outside the external flap 140c of the incision 140a, an abnormal behavior of the intraocular lens may occur when the intraocular lens is ejected through the distal end opening member 100a.

In this case, when the user inserts the intraocular lens insertion apparatus 1 into the eyeball of the patient through the incision 140a of the cornea 140, the user can check whether the intraocular lens insertion apparatus 1 is inserted to the position at which the indicator 150 on the distal end member 10a of the nozzle body 10 overlaps the internal flap 140b of the incision 140a to determine whether the insertion length of the intraocular lens insertion apparatus 1 inserted through the incision 140a is adequate. When the indicator 150 is on the side of the external flap 140c with respect to the internal flap 140b or outside the external flap 140c in the top view of the distal end member 10a of the intraocular lens insertion apparatus 1, the user pushes the intraocular lens insertion apparatus 1 toward the eyeball. As a result, since the user can modify the position of the intraocular lens insertion apparatus 1 to achieve that the indicator 150 overlaps the internal flap 140b as illustrated in FIG. 13, the user can properly control the insertion length of the intraocular lens insertion apparatus 1 inserted through the incision 140a.

It is noted in the above examples that the distal end member 10a is configured so that the shape of the distal end member 10a in the top view is approximately a rectangle or a square when the distal end member 10a of the intraocular lens insertion apparatus 1 projects from the internal flap 140b of the incision 140a. However, the distal end member 10a can be configured so that the shape of the distal end member 10a in the top view is approximately a semiellipse or a semicircle when the distal end member 10a of the intraocular lens insertion apparatus 1 projects from the internal flap 140b of the incision 140a. With such a configuration, the user can determine whether the insertion length of the intraocular lens insertion apparatus 1 is adequate based on the relation between the length of the intraocular lens insertion apparatus 1 in the insertion direction and the length of the intraocular lens insertion apparatus 1 in the direction perpendicular to the insertion direction regarding the part of the distal end member 10a which projects from the internal flap 140b of the incision 140a.

Although the indicator 150 is a mark printed on the surface of the distal end member 10a of the nozzle body 10 in the above modification, a variety of conventional indicators can be provided for the distal end member 10a instead by, for example, forming a convex part, a concave part or an uneven part on the surface or by, for example, forming a rough surface or a colored surface in the area ranging from the indicator to the tip of the distal end member 10a or in the area ranging from the indicator to the rear end of the distal end member 10a, as long as the user can visually check the indicators which can be used for aligning the indicators with the internal flap of the incision of the cornea and for determining whether the insertion length of the intraocular lens insertion apparatus 1 is adequate.

Further, the indicators in the above embodiments and modifications are used as means for indicating that the entire distal end opening member 100a is inside the cornea 140 with respect to the external flap 140c of the incision 140a. The state in which the entire distal end opening member 100a is inside the cornea 140 with respect to the external flap 140c of the incision 140a includes not only a state in which no part of the distal end opening member 100a exists outside the external flap 140c of the incision 140a but also a state in which although a part of the distal end opening member 100a exists outside the external flap 140c of the incision 140a the area of the distal end opening member 100a outside the external flap 140c is practically small so that an abnormal behavior of the intraocular lens does not occur.

REFERENCE SIGNS LIST 1 insertion apparatus
2 intraocular lens
10 nozzle body
10a distal end member of nozzle body
10b rear end member of nozzle body
10c through-hole
100 insertion tube
100a distal end opening member
100b distal end area
100c projecting member
100d rear end area
100e body member

What is claimed is:

1. An intraocular lens insertion apparatus comprising:
a distal end member which is inserted through an incision in an eyeball of a patient;
an opening member provided for the distal end member through which an intraocular lens is ejected; and
an indicator provided for the distal end member configured to indicate that an entire part of the opening member is inside a cornea of the eyeball or inside a sclerocornea of the eyeball with respect to an external flap of the incision,
wherein the indicator indicates that the entire part of the opening member is inside the cornea of the eyeball or inside the sclerocornea of the eyeball based on a relation, in a top view of the distal end member of the intraocular lens set in the intraocular lens insertion apparatus, between (a) a length of a part of the distal end member in an insertion direction of the distal end member inserted into the incision and (b) a length of a part of the distal end member in a direction perpendicular to the insertion direction, wherein the part of the distal end member is a part projected from an internal flap of the incision into the eyeball.

2. The intraocular lens insertion apparatus according to claim 1, wherein the indicator indicates that the entire part of the opening member is inside the cornea of the eyeball or inside the sclerocornea of the eyeball with respect to the external flap of the incision when the length of the distal end member in the insertion direction is longer than the length of the distal end member in the direction perpendicular to the insertion direction.

3. The intraocular lens insertion apparatus according to claim 1, wherein
the indicator is an indicator provided for a surface of the distal end member, and
when the distal end member is inserted through the incision, the entire part of the opening member inside the cornea or inside the sclerocornea with respect to the external flap of the incision in a state in which the indicator provided for the distal end member almost overlaps the internal flap of the incision or is inside the internal flap in the top view.

* * * * *